United States Patent [19]

Chang et al.

[11] Patent Number: 5,475,179
[45] Date of Patent: Dec. 12, 1995

[54] REGIOSELECTIVE PRODUCTION OF PARA-DIALKYL BENZENES

[75] Inventors: Clarence D. Chang, Princeton; Paul G. Rodewald, Rocky Hill, both of N.J.

[73] Assignee: Mobil Oil, Fairfax, Va.

[21] Appl. No.: 233,542

[22] Filed: May 5, 1994

Related U.S. Application Data

[63] Continuation of Ser. No. 38,310, Mar. 29, 1993, abandoned, which is a continuation-in-part of Ser. No. 850,104, Mar. 12, 1992, abandoned.

[51] Int. Cl.$^6$ .................................................. C07C 5/52
[52] U.S. Cl. ........................................ 585/475; 585/467
[58] Field of Search .................................. 585/467, 475

[56] References Cited

U.S. PATENT DOCUMENTS

| | | | |
|---|---|---|---|
| 3,682,996 | 8/1972 | Kerr | 556/173 |
| 3,698,157 | 10/1972 | Allen et al. | 95/84 |
| 4,090,981 | 3/1978 | Rodewald | 252/455 Z |
| 4,127,616 | 11/1978 | Rodewald | 585/467 |
| 4,145,315 | 3/1979 | Rodewald | 252/455 Z |
| 4,283,306 | 8/1981 | Herkes | 252/432 |
| 4,465,886 | 8/1984 | Rodewald | 585/467 |
| 4,477,583 | 10/1984 | Rodewald | 502/71 |
| 4,843,057 | 6/1989 | D'Amore et al. | 502/263 |
| 4,851,604 | 7/1989 | Absil et al. | 585/475 |
| 4,927,979 | 5/1989 | Yamagishi et al. | 568/791 |
| 4,950,835 | 8/1990 | Wang et al. | 585/467 |

FOREIGN PATENT DOCUMENTS 296582 12/1988 European Pat. Off. .

OTHER PUBLICATIONS

Hibino, et al., "Shape Selectivity Over HZSM-5 Modified by Chemical Vapor Deposition of Silicone Alkoxide," Journal of Catalysis, 12, 551–558 (1991).

*Primary Examiner*—P. Achutamurthy
*Attorney, Agent, or Firm*—Alexander J. McKillop; Dennis P. Santini; Edward F. Kenehan, Jr.

[57] ABSTRACT

A method for the selective disproportionation of a substituted aromatic compound wherein the aromatic compound is passed over a catalytic molecular sieve which has been pre-selectivated with a silicon deposit and then subsequently treated with a silicon-containing, high efficiency p-xylene selectivating agent at conversion conditions. The present invention attains para-xylene product over 95% at a toluene conversion of at least 20%. The present invention also includes the highly para-selective catalyst which results from the pre-selectivation and subsequent treatment of a catalytic molecular sieve with a high efficiency p-xylene selectivating agent under the recited conditions.

14 Claims, 4 Drawing Sheets

REGIOSELECTIVE PRODUCTION OF PARA-DIALKYL BENZENES

CROSS REFERENCE TO RELATED APPLICATION

This application is a continuation of U.S. application Ser. No. 08/038,310, filed Mar. 29, 1993, now abandoned, which is a continuation-in-part of U.S. patent application Ser. No. 07/850,104, filed Mar. 12, 1992.

BACKGROUND

The present invention is directed to a process and catalyst for the regioselective production of para-substituted compounds, e.g. para-xylene. One aspect of the present invention includes a process wherein a feedstock which includes an aromatic hydrocarbon and a high efficiency, p-xylene selectivating agent are co-fed over a pre-selectivated catalytic molecular sieve.

Para-xylene is a very valuable commercial product useful in the production of polyester fibers. The catalytic production of para-xylene has received much attention in the scientific community and various methods for increasing catalyst para-selectivity have been described.

The synthesis of para-xylene is typically performed by methylation of toluene over a catalyst under conversion conditions. Examples are the reaction of toluene with methanol as described by Chen et al., J. Amer. Chem. Sec. 1979, 101, 6783, and toluene disproportionation, as described by Pines in "The Chemistry of Catalytic Hydrocarbon Conversions", Academic Press, New York, 1981, p. 72. Such methods typically result in the production of a mixture including para-xylene, ortho-xylene, and meta-xylene. Depending upon the para-selectivity of the catalyst and the reaction conditions, different percentages of para-xylene are obtained. The yield, i.e., the amount of feedstock actually converted to xylene, is also affected by the catalyst and the reaction conditions.

Previously known toluene methylation reactions typically provide many by-products such as those indicated in the following formula:

Thermodynamic Equilibria for Toluene Conversion to the Products Indicated

One known method for increasing para-selectivity of zeolite catalysts is to modify the catalyst by treatment with "selectivating agents". Modification methods have been suggested wherein the catalyst is modified by treatment prior to use to provide a silica coating. For example, U.S. Pat. Nos. 4,477,583 and 4,127,616 disclose methods wherein a catalyst is contacted at ambient conditions with a modifying compound such as phenymethyl silicone in a hydrocarbon solvent or an aqueous emulsion, followed by calcination. Such modification procedures have been successful in obtaining para-selectivity, i.e., para-xylene/all xylenes, of greater than about 90% but with commercially unacceptable toluene conversions of only about 10%, resulting in a yield of not greater than about 9%, i.e., 10%×90%. Such processes also produce significant quantities of ortho-xylene and meta-xylene thereby necessitating expensive separation processes in order to separate the para-xylene from the other isomers.

Typical separation procedures comprise costly fractional crystallization and adsorptive separation of para-xylene from other xylene isomers which are customarily recycled. Xylene isomerization units are then required for additional conversion of the recycled xylene isomers into an equilibrium mixture comprising para-xylene.

Those skilled in the art appreciate that the expense of the separation process is proportional to the degree of separation required. Therefore, significant cost savings are achieved by increasing selectivity to the para-isomer while maintaining commercially acceptable conversion levels.

It is, therefore, highly desirable to provide a regioselective process for the production of para-xylene from toluene while maintaining commercially acceptable toluene conversion levels.

SUMMARY OF THE INVENTION

One process of the present invention comprises the regioselective conversion of toluene to para-xylene by disproportionating toluene in a reaction stream containing a toluene feed with a pre-selectivated catalytic molecular sieve and reaction conditions to provide a single pass, para-xylene purity of at least about 90%. As used herein, the term "para-xylene purity" means the percentage of para-xylene in all of the $C_8$ products which include ethylbenzene, para-xylene, ortho-xylene, and meta-xylene. Those skilled in the art will appreciate that the proximity of the boiling points of $$\text{Yield} = \text{Selectivity} \times \text{Conversion} = \frac{9.64}{101.35} \times 0.55 = 5.23 \text{ wt \%}$$

$$\text{p-Xylene Yield} = 100 \times \frac{9.64}{184.27} = 5.23 \text{ wt \%}$$

p-Xylene Purity (p-Xylene/all $C_8$'s) = 21.45 wt % these $C_8$ products necessitates more expensive separation processes whereas para-xylene may be more readily separated from other components in the product stream such as benzene, toluene, and para-ethyltoluene.

The present invention also comprises a method for the regioselective production of para-xylene by passing a reaction stream which contains an aromatic feedstock, e.g., toluene, in a single pass, over a pre-selectivated catalytic molecular sieve in the presence of hydrogen at reaction conditions suitable to provide para-xylene purity of greater than about 90%. The product stream also includes small amounts of ortho- and meta-xylene and trace amounts of impurities such as ethylbenzene. As used herein, the term "xylene product" indicates the total amount of xylenes resulting from the disproportionation reaction.

One particular aspect of the present invention comprises co-feeding an aromatic feedstock over a pre-selectivated catalytic molecular sieve with a high efficiency, p-xylene selectivating agent at conversion conditions suitable for converting toluene to xylene. In one embodiment of the present invention, the toluene is fed simultaneously with a high-efficiency selectivating agent and hydrogen at reaction conditions until the desired p-xylene selectivity is attained, whereupon the feed of selectivating agent is discontinued. This co-feeding of selectivating agent with toluene will hereinafter be termed "trim selectivation". Reaction conditions for this trim-selectivation step generally include a temperature of about 350°–540° C. and a pressure of about atmospheric–5000 psig. The feed is provided to the system at a rate of about 0.1–20 WHSV. The hydrogen is fed at a hydrogen to hydrocarbon molar ratio of about 0.1–20.

The high efficiency para-xylene selectivating agent preferably comprises a silicon containing compound. For example, organic silicones, siloxanes, polysiloxanes, silanes and mixtures thereof are suitable. According to one preferred embodiment of the present invention, a silicone containing phenylmethylsilicon and dimethylsilicon groups in a ratio of about 1:1 is co-fed to the system, while the other components, e.g., toluene and hydrogen, are fed in the amounts set forth above. The high-efficiency para-xylene selectivating agent is fed in an amount of about 0.1%–50% of the toluene according to this preferred embodiment. Depending upon the percentage of selectivating agent used, the trim selectivation will preferably last for less than one week, most preferably less than 24 hours.

Embodiments of the present invention have been successful in attaining para-xylene purity of over 99% at toluene conversion rates of at least 15%, preferably at least about 20–25%. One alternative embodiment of the present invention includes stopping the co-feed of the high-efficiency para-xylene selectivating agent while continuing the disproportionation reaction.

The present invention achieves higher para-xylene purity at commercially acceptable conversion rates than previously disclosed processes. The present invention thus allows for a significant reduction in process costs previously associated with the separation of unwanted by-products. Processes of the prior art typically require expensive secondary and tertiary treatment procedures in order to obtain these efficiencies.

Consequently, the present invention provides unique reactions having increased para-xylene product. The highly para-selective catalyst which is obtained when the pre-selectivated catalytic molecular sieve is treated with a high efficiency para-xylene selectivating agent in the manner set forth above is also included in the present invention.

The present invention also includes additional methods for modifying a catalytic molecular sieve in order to reduce the production of unwanted by-products during the selective disproportionation of toluene to p-xylene and the resulting catalytic molecular sieves.

As explained in greater detail below, the present invention provides a method for obtaining para-xylene at conversion rates of at least about 20% and with para-xylene purity of greater than 90%, preferably at least 95%, and most preferably about 99%.

DETAILED DESCRIPTION

The present invention is an improvement to the invention disclosed in a commonly-owned co-pending U.S. patent application Ser. No. 850,104 filed Mar. 12, 1992 and entitled "Regioselective Methylation of Toluene to Para-Xylene", and its continuation-in-part U.S. patent application Ser. No. 08/024,972 (Attorney's Docket 6962S) filed Mar. 2, 1993, now abandoned. The co-pending applications are incorporated by reference.

The methylation reaction of the present invention is described herein in terms of disproportionation. However, the present invention also applies to other methylation reactions such as those using methylhalides and methylethers. Normally a single pass conversion of a toluene stream results in a product stream which includes dimethylbenzenes having alkyl groups at all locations, i.e., ortho-, meta-, and para-xylenes. Furthermore, the xylenes are known to proceed in a reaction which produces unwanted ethylbenzenes (EB) by the following reaction:

Until the present invention, the purity of p-xylene with respect to all of the $C_8$ products in a single pass has been limited to less than 90% when isomerization is permitted. This efficiency is reduced somewhat by the production of ethylbenzene.

The present invention, however, provides high efficiency conversion which reduces production of ortho- and meta-isomers to the benefit of the desired para-isomer. The resulting product stream contains greater than 90% para-xylene. For example, the ortho-xylene isomer can be reduced to not more than about 0.5% of the total xylenes content while the meta-xylene isomer can be reduced to less than about 5% of the total xylene content. Moreover, when the reaction system is properly treated, such as by deposition of platinum on the molecular sieve, the presence of ethylbenzene can be reduced to less than about 0.3% of the $C_8$ product.

The catalyst of the present invention is pre-selectivated ex situ and subsequently "trim selectivated" with a high efficiency para-xylene selectivating agent. The selectivating agent advantageously increases the paraselectivity of the catalyst and, therefore, the efficiency of para-xylene production during the conversion of toluene to xylene. As used herein, the term "high efficiency, p-xylene selectivating agent" is used to indicate substances which will increase the para-selectivity of a catalytic molecular sieve to the stated levels while maintaining commercially acceptable toluene to xylene conversion levels. Such substances include, for example, volatile organosilicon compounds with sufficient vapor pressure for proper deposition under conversion conditions, i.e., temperature ranging from about 100° C. to about 600° C., preferably from about 300° C. to about 500° C.; pressures ranging from about 0 to about 2000 psig, preferably from about 15 to about 800 psig; a mole ratio of hydrogen to hydrocarbons from about 0 (i.e. no hydrogen is present) to about 10, preferably from about 1 to about 4; at a weight hourly space velocity (WHSV) from about 0.1 to about 100 hr$^{-1}$, preferably from about 0.1 to about 10 hr$^{-1}$. It is preferred that the organosilicon compound have a kinetic diameter greater than that of the largest pore of the zeolite. Upon thermolysis, a siliceous coating is deposited on the zeolite surface, eliminating surface activity and enhancing shape-selectivity.

The selectivation of the catalyst is preferably performed with a silicone containing compound. An example of silicone compounds which can be used in the present invention can be characterized by the general formula:

where $R_1$ is hydrogen, fluorine, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethylsilicone, diethylsilicone, phenylmethylsilicone, methylhydrogensilicone, ethylhydrogensilicone, phenylhydrogensilicone, methylethylsilicone, phenylethylsilicone, diphenylsilicone, methyltrifluoropropylsilicone, ethyltrifluoropropylsilicone, tetrachlorophenylmethyl silicone, tetrachlorophenylethyl silicone, tetrachlorophenylhydrogen silicone, tetrachlorophenylphenyl silicone, methylvinylsilicone and ethylvinylsilicone. The silicone compound need not be linear but may be cyclic as for example hexamethylcyclotrisiloxane, octamethylcyclotetrasiloxane, hexaphenylcyclotrisiloxane and octaphenylcyclotetrasiloxane. Mixtures of these compounds may also be used as well as silicones with other functional groups. Other silicon-containing compounds, such as silanes, may also be utilized.

Useful siloxanes or polysiloxanes include as non-limiting examples hexamethylcyclotrisiloxane, octamethylcyclotetrasiloxane, decamethylcyclopentasiloxane, hexamethyldisiloxane, octamethytrisiloxane, decamethyltetrasiloxane, hexaethylcyclotrisiloxane, octaethylcyclotetrasiloxane, hexaphenylcyclotrisiloxane and octaphenylcyclotetrasiloxane.

Useful silanes, disilanes or alkoxysilanes include organic substituted silanes having the general formula:

wherein R is a reactive group such as hydrogen, alkoxy, halogen, carboxy, amino, acetamide, trialkylsilyl. $R_1$, $R_2$ and $R_3$ can be the same as R or an organic radical which may include alkyl of from 1 up to about 40 carbon atoms, alkyl or aryl carboxylic acid wherein the organic portion of the alkyl contains about 1 to 30 carbon atoms and the aryl group contains about 6 to 24 carbon atoms, aryl groups of about 6 to 24 carbons which may be further substituted, alkylaryl and arylalkyl groups containing about 7 up to about 30 carbon atoms. Preferably, the alkyl group of an alkyl silane is between 1 and 4 carbon atoms in chain length. Mixtures may also be used.

The silanes or disilanes include, as non-limiting examples, dimethylphenylsilane, phenytrimethylsilane, triethylsilane and hexamethyldisilane. Useful alkoxysilanes for trim selectivation are those with at least one silicon-hydrogen bond.

For pre-selectivation the silicon compound is deposited on the external surface of the catalyst by any suitable method. For example, the silicon may be dissolved in a solvent, mixed with the catalyst, and then dried. The silicon compound employed may be in the form of a solution, a liquid or a gas under the conditions of contact with a zeolite. Examples of methods of depositing silicon on the surface of the zeolite are found in U.S. Pat. Nos. 4,090,981, 4,127,616, 4,465,886 and 4,477,583 to Rodewald, which are incorporated by reference herein.

Following deposition of the silicon-containing compound in pre-selectivation, the catalyst is preferably calcined. For example, the catalyst may be calcined in an oxygen-containing atmosphere, preferably air, at a rate of 0.2° to 5° C./minute to a temperature greater 300° C. but below a temperature at which the crystallinity of the zeolite is adversely affected. Generally, such temperature will be below 600° C. Preferably the temperature of calcination is within the approximate range of 350° to 550° C. The product is maintained at the calcination temperature usually for 1 to 24 hours.

The present invention includes processes for the selective disproportionation of a toluene feedstock into para-xylene utilizing a high efficiency para-xylene selectivating agent. Preferably, the kinetic diameter of the high efficiency, p-xylene selectivating agent is larger than the zeolite pore diameter, in order to avoid reducing the internal activity of the catalyst. The selectivating agent advantageously increases the para-selectivity of the catalyst and, therefore, the efficiency of para-xylene production during the conversion of toluene to xylene. As used herein, the term "xylene product" indicates the total amount of xylenes resulting from the disproportionation reaction. The term "high efficiency, p-xylene selectivating agent" is used to indicate substances which will increase the para-selectivity of a catalytic molecular sieve to the stated levels while maintaining commercially acceptable conversion rates. The word "para-xylene" in this term is not intended to limit the scope of the present invention to the production of xylenes since other para-substituted aromatics may be produced. Such substances include, for example, organic silicon compounds such as phenylmethyl silicone, dimethylsilicone, and blends thereof, which have been found to be suitable. Other silicon-containing compounds such as those listed above may also be utilized.

While not wishing to be bound by theory, it is believed that the advantages of the present invention are obtained by rendering acid sites on the external surfaces of the catalyst substantially inaccessible to reactants while increasing catalyst tortuosity. Acid sites existing on the external surface of the catalyst are believed to isomerize the para-xylene exiting the catalyst pores back to an equilibrium level with the other two isomers thereby reducing the amount of para-xylene in the xylenes to only about 24%. By reducing the availability of these acid sites to the para-xylene exiting the pores of the catalyst, the relatively high level of para-xylene can be maintained. It is believed that the high-efficiency, p-xylene selectivity agents of the present invention block or otherwise render these external acid sites unavailable to the para-xylene by chemically modifying said sites.

In line with this theory, it is also believed that the presence of hydrogen in the reaction zone during the trim selectivation is important in order to maintain the desired high yields of para-xylene when a silicone compound is used as the high-efficiency para-xylene selectivating agent. The importance of the hydrogen may be reduced in alternative embodiments by using a high efficiency para-xylene selectivating agent comprising silane or some other compound which effectively renders the isomerizing acid sites on the external surface of the catalyst inaccessible.

One process of the present invention utilizes a high efficiency para-xylene selectivating agent which include a silicon compound wherein the silicon compound is introduced by co-feeding, for example, at least one silicon compound with the toluene feedstock over a conversion catalyst at reaction conditions until the desired degree of selectivation is achieved, at which time the feed of selectivity agent may be discontinued.

The toluene feedstock preferably includes about 50% to 100% toluene, more preferably at least about 80% toluene in the toluene feedstock. Other compounds such as benzene, xylenes, and trimethylbenzene may also be present in the toluene feedstock without adversely affecting the present invention.

According to the processes of this invention, the toluene feedstock may also be dried, if desired, in a manner which will minimize moisture entering the reaction zone. Methods known in the art suitable for drying the toluene charge for the present process are numerous. These methods include percolation through any suitable dessicant, for example, silica gel, activated alumina, molecular sieves or other suitable substances, or the use of liquid charge dryers.

The catalytic molecular sieves of the present invention are in the hydrogen form and preferably comprise an intermediate pore-size zeolite such as a ZSM-5, ZSM-11, ZSM-22, ZSM-23, or ZSM-35. The catalyst of the present invention preferably has an alpha value greater than 100, for example about 150–2000, and a silica-alumina ratio less than 100 preferably about 20–80. The Alpha Value of the catalyst may be increased by treating the catalyst with nitric acid or by mild steaming as discussed in U.S. Pat. No. 4,326,994. The Alpha Value is an approximate indication of the catalytic cracking activity of the catalyst compared to a standard catalyst and it gives the relative rate constant (rate of normal hexane conversion per volume of catalyst per unit time.) It is based on the activity of the amorphous silica-alumina cracking catalyst taken as an Alpha of 1 (Rate Constant= 0.016 sec$^{-1}$). The Alpha Test is described in U.S. Pat. No. 3,354,078 and in *The Journal of Catalysis*, Vol. 4, pp. 522–529 (August 1965): Vol. 6, p. 278 (1966); and Vol. 61, p. 395 (1980), each incorporated herein by reference as to that description. It is noted that intrinsic rate constants for many acid-catalyzed reactions are proportional to the Alpha Value for a particular crystalline silicate catalyst (see "The Active Site of Acidic Aluminosilicate Catalysts," *Nature*, Vol. 309, No. 5959, pp. 589–591, 14 Jun. 1984). The experimental conditions of the test used herein include a constant temperature of 538° C. and a variable flow rate as described in detail in the *Journal of Catalysis*, Vol. 61, p. 395. The catalytic molecular sieves also preferably have an initial Constraint Index of about 1–12 and a Constraint Index of about 1–30 after selectivation. The method by which Constraint Index is determined is described fully in U.S. Pat. No. 4,016,218, incorporated herein by reference for details of the method. The crystal size of zeolites used herein is preferably greater than 0.1 micron.

For the improved disproportionation process of this invention, the suitable molecular sieve may be employed in combination with a support or binder material such as, for example, a porous inorganic oxide support or a clay binder. While the preferred binder is silica, other non-limiting examples of such binder materials include alumina, zirconia, magnesia, thoria, titania, boria and combinations thereof, generally in the form of dried inorganic oxide gels or gelatinous precipitates. Suitable clay materials include, by way of example, bentonite and kieselguhr. The relative proportion of suitable crystalline molecular sieve to the total composition of catalyst and binder or support may be about 30 to about 90 percent by weight and is preferably about 50–80 percent by weight of the composition. The composition may be in the form of an extrudate, beads or fluidizable microspheres.

Operating conditions employed in the improved process of the present invention will affect the para-selectivity and toluene conversion rate. Such conditions include the temperature, pressure, space velocity, molar ratio of the reactants, and the hydrogen to hydrocarbon mole ratio. One preferred embodiment of the present invention includes contacting a catalytic molecular sieve with a toluene feedstock which includes a silicone compound under conditions for effecting vapor-phase disproportionation. Conditions effective for accomplishing the high para-selectivity and acceptable toluene disproportionation conversion rates include a reactor inlet temperature of about 350°–540° C., preferably greater than about 400° C., a pressure of about atmospheric –5000 psig, preferably about 100 to 1000 psig, a WHSV of about 0.1–20, preferably about 2–4, and a hydrogen to hydrocarbon mole ratio of about 0.1–20, preferably about 2–4. This process may be conducted in either batch or fluid bed operation with attendant benefits of either operation readily obtainable.

The effluent is separated and distilled to remove the desired product, i.e., para-xylene, plus other by-products. The unreacted reactant, i.e. toluene, is preferably recycled for further reaction. The benzene is a valuable co-product.

In accordance with another embodiment of the present invention, the catalyst is further modified in order to reduce the amount of undesirable by-products, particularly ethylbenzene. The state of the art is such that the reactor effluent from toluene disproportionation typically contains about 0.5% ethylbenzene by-product. Upon distillation of the reaction products, the level of ethylbenzene in the $C_8$ fraction often increases to about 3–4 percent. This level of ethylbenzene is unacceptable for polymer grade p-xylene since ethylbenzene in the $C_8$ product, if not removed, degrades the quality of fibers ultimately produced from the p-xylene product. Consequently, ethylbenzene content must be kept low. The specification for ethylbenzene in the $C_8$ product has been determined by industry to be less than 0.3%. Ethylbenzene can be substantially removed by isomerization or by superfractionation processes. Removal of the ethylbenzene by conventional isomerization would be impractical with the present invention since the xylene stream, which includes greater than 90% para-xylene, would be concurrently isomerized to equilibrium xylenes reducing the amount of para-xylene in this xylene stream to about 24%. And it is known in the art that the alternative procedure of removing the ethylbenzene by superfractionation is extremely expensive.

In order to avoid the need for downstream ethylbenzene removal, the level of ethylbenzene by-product is advantageously reduced by incorporating a hydrogenation-dehydrogenation function in the catalyst, such as by addition of a metal compound such as platinum. While platinum is the preferred metal, other metals such as palladium, nickel, copper, cobalt, molybdenum, rhodium, ruthenium, silver, gold, mercury, osmium, iron, zinc, cadmium, and mixtures thereof may be utilized. The metal may be added by cation exchange, in amounts of about 0.01–2%, typically about 0.5%. The metal must be able to enter the pores of the catalyst in order to survive a subsequent calcination step. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate to increase activity. The metallic compound advantageously enters the pores of the catalyst. The catalyst can then be filtered, washed with water and calcined at temperatures of about 250° to 500° C.

By the present process, toluene can be converted to aromatic concentrates of high value, e.g., about 99% para-xylene based on all $C_8$ products. In a typical embodiment of the present process, optimum toluene conversion is found to be about 20–25 weight percent with a para-xylene product of about 90–99%.

The following specific examples will serve to further illustrate the processes, catalysts, and some advantages of the present invention, without unduly limiting same. As basis for comparison, a toluene feedstock was disproportionated in Example 1 utilizing a high-efficiency, para-xylene selectivity agent without pre-selectivating the catalyst.

EXAMPLE 1

Figure 1:
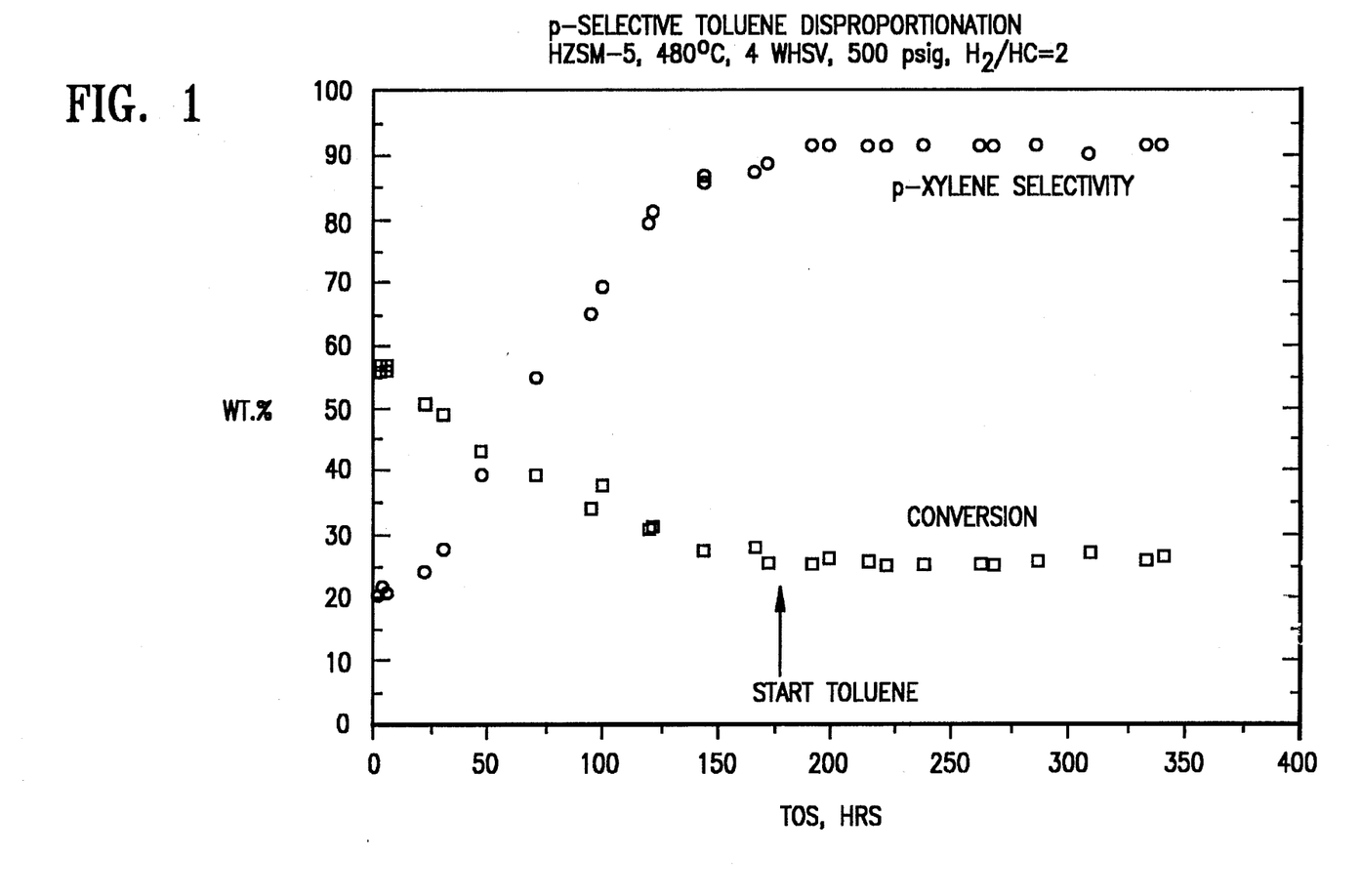
FIG. 1 is a graph indicating the para-selectivity and toluene conversion over a non-preselectivated catalyst.

Trim selectivation of HZSM-5 was carried out in a fixed-bed reactor using 2.00 g catalyst (silica bound) and 1% phenylmethyl silicone in toluene feed at 480° C., 500 psig, 4.0 WHSV, and hydrogen/hydrocarbon ratio=2. Table 1 and FIG. 1 show toluene conversion and para-xylene selectivity for HZSM-5 as a function of time on stream.

TABLE 1

| Silicone Selectivation of HZSM-5 | | |
|---|---|---|
| Time on Stream, hrs | Toluene Conversion, wt % | Para-xylene in Xylenes, wt % |
| 1 | 56 | 22 |
| 6 | 57 | 21 |

TABLE 1-continued

| Silicone Selectivation of HZSM-5 | | |
|---|---|---|
| Time on Stream, hrs | Toluene Conversion, wt % | Para-xylene in Xylenes, wt % |
| 22 | 51 | 24 |
| 46 | 42 | 39 |
| 98 | 36 | 70 |
| 143 | 28 | 86 |
| 170 | 25 | 89 |

Silicone selectivation substantially increased para-xylene selectivity from 22% to 89%. For HZSM-5, 89% para-xylene selectivity was achieved after 170 hours selectivation. Feed was then changed to 100% toluene. The para-selectivity and conversion lined out at about 89% and 25%, respectively.

EXAMPLE 2

A silica modified HZSM-5 was prepared by adding 5.00 g HZSM-5 to 1.26 g phenylmethylpolysiloxane dissolved in 40 cc hexane. The solvent was distilled and the catalyst was air calcined at 1° C./min to 538° C., then 6 hours at 538° C. The catalyst contained a nominal 10% added silica.

Figure 2:
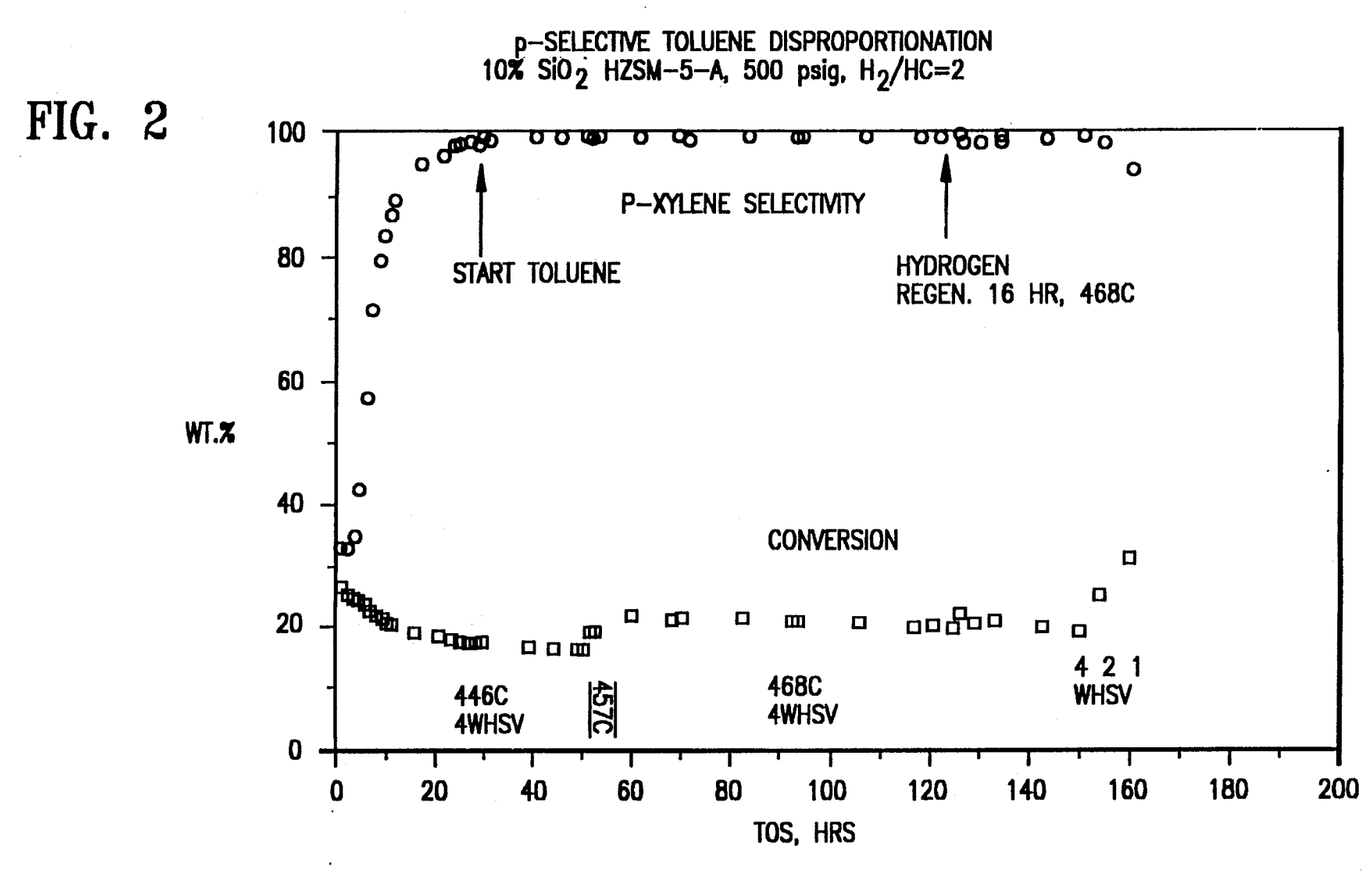
FIG. 2 depicts para-selectivity and conversion rates for a zeolite which has been pre-selectivated with 10% $SiO_2$.

Silicone trim selectivation of the 10% $SiO_2$-HZSM-5 was carried out at 446° C., 500 psig, 4.0 WHSV, and hydrogen/hydrocarbon ratio=2. Table 2 and FIG. 2 show toluene conversion and para-xylene selectivity for 10% $SiO_2$-HZSM-5 as a function of time on stream.

TABLE 2

| Silicone Selectivation of 10% $SiO_2$-HZSM-5 | | |
|---|---|---|
| Time on Stream, hrs | Toluene Conversion, wt % | Para-xylene in Xylenes, wt % |
| 2 | 25 | 33 |
| 4 | 24 | 43 |
| 6 | 23 | 72 |
| 8 | 21 | 84 |
| 10 | 21 | 89 |
| 15 | 19 | 94 |
| 20 | 18 | 96 |
| 28 | 18 | 98 |

The silicone trim selectivation substantially increased para-xylene selectivity from 33% to 98% over 28 hours on stream. Feed was then changed to 100% toluene. Over the next ten hours the selectivity increased to 99% at 16% conversion. To further increase conversion, the temperature was increased to 457° C. and shortly thereafter to 468° C. The conversion rose to 21%, then decreased slightly to 20% over the next 80 hours. The para-xylene selectivity increased from 99.2% to 99.6% over the same 80 hours.

Compared to the HZSM-5 at Example 1, the 10% $SiO_2$-HZSM-5 catalyst showed a substantially higher selectivation rate. For silica-modified HZSM-5, 89% para-xylene selectivity was achieved after only 10 hours on stream (17 times faster than the 170 hours for the HZSM-5 parent). Also, the time needed to reach optimum para-selectivation, 1 day for $SiO_2$-HZSM-5 compared to 1 week for HZSM-5, was shorter despite the higher selectivation temperature for HZSM-5(480° C. vs. 446° C.).

The total phenylmethyl silicone consumption was 6.80 g silicone per g HZSM-5 and 1.42 gram of silicone per gram of $SiO_2$-HZSM-5. Thus selectivation of $SiO_2$-HZSM-5 consumed nearly five (4.79) times less silicone than selectivation of HZSM-5 and therein shows a catalyst cost advantage.

A 1% solution of silicone in toluene may not be optimal, i.e., a more rapid or a slower selectivation may in principle be obtained by increasing or decreasing the wt % silicone in the feed. Also, although phenylmethyl silicone was used in this study, other silicones and organosilicon compounds may be effective selectivation materials.

EXAMPLE 3

Figure 3:
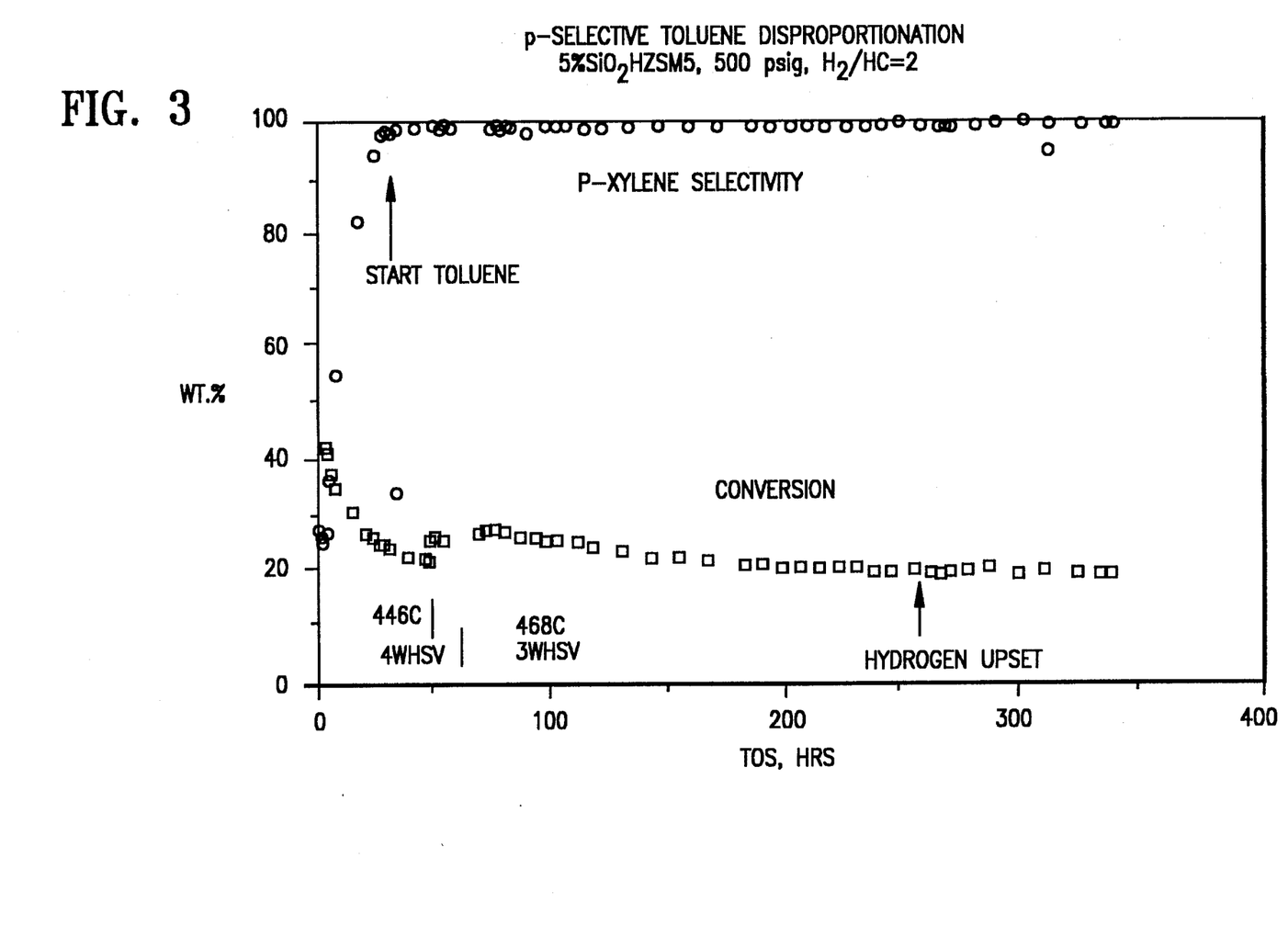
FIG. 3 provides para-selectivity and conversion rates for a zeolite which has been pre-selectivated with 5% $SiO_2$.

Silicone trim selectivation of 5% $SiO_2$-HZSM-5 was carried out at 446° C., 500 psig, 4.0 WHSV, and hydrogen/hydrocarbon ratio=2. The 5% $SiO_2$ catalyst was more active than the 10% $SiO_2$ catalyst and was expected to produce a more active selectivated catalyst. Table 3 and FIG. 3 show toluene conversion and para-xylene selectivity for 5% $SiO_2$-HZSM-5 as a function of time on stream.

TABLE 3

Silicone Selectivation of 5% $SiO_2$-HZSM-5

| Time on Stream, hrs | Toluene Conversion, wt % | para-xylene in Xylenes, wt % |
|---|---|---|
| 2 | 41 | 25 |
| 4 | 41 | 27 |
| 5 | 38 | 36 |
| 7 | 35 | 54 |
| 14 | 31 | 83 |
| 21 | 27 | 95 |
| 26 | 25 | 98 |

Silicone selectivation substantially increased para-xylene selectivity from 25% to 98% over 26 hours on stream. Compared to 10% $SiO_2$-HZSM-5, the 5% $SiO_2$ catalyst showed consistently higher conversion over the one day selectivation time. Feed was then changed to 100% toluene. Over the next 6 hours the selectivity increased to 99% at 24% conversion, temperature was increased to 468° C. and WHSV was decreased to 3. Conversion increased to 27%, then gradually decreased to and remained constant at 21% for 6 days (146 hours). Correspondingly, the para-xylene selectivity was initially unchanged at 99% then gradually increased to and remained constant at 99.6%–99.9% for 6 days when the run was arbitrarily terminated.

EXAMPLE 4

A 0.05% Pt-10% $SiO_2$-HZSM-5 catalyst was prepared by adding 2.50 g of the 10% $SiO_2$-HZSM-5 prepared in EXAMPLE 2 to 12.5 cc 1M ammonium nitrate solution. After 1.5 hours, a solution of 0.0025 g tetraamine platinum(II)nitrate in approximately 0.5 cc water was added. After standing overnight the catalyst was filtered, washed with water, and air calcined at 5° C./min to 350° C., then 3 hours at 350° C.

Toluene disproportionation was carried out over 2.00 g of the catalyst of Example 4 at 446° C., 500 psig, 4 WHSV, and a hydrogen/hydrocarbon mole ration of 2.0. Table 4 shows the product distribution compared to that of Pt-free silica-modified HZSM-5 from Example 2 tested under the same operating conditions. At similar toluene conversion, the ethylbenzene product was reduced by nearly a factor of 12 using the Pt-catalyst. The undesirable $C_9^+$ aromatics product also was reduced by nearly a factor of 2.

TABLE 4

| Component, wt % | Pt—$SiO_2$-HZSM-5 | $SiO_2$-HZSM-5 |
|---|---|---|
| Benzene | 45.84 | 41.65 |
| Ethylbenzene | 0.05 | 0.59 |
| Xylenes | 43.12 | 55.98 |
| $C_{9+}$ Aromatics | 0.99 | 1.78 |
|  | 100.00 | 100.00 |
| Ethylbenzene in $C_8$, wt. | 0.10 | 1.18 |
| p-Xylene in Xylenes, wt % | 25.8 | 29.8 |
| Toluene Conversion, wt % | 35 | 34 |

EXAMPLE 5

The catalyst of Example 4 was treated in situ with a 1% solution of phenymethylpolysiloxane in toluene at 446° C., 500 psig, 4 WHSV, and a hydrogen/hydrocarbon mole ratio of 2.0. After 32 hours on stream the feed was changed to 100% toluene. Table 5 shows the product distribution compared to that of Pt-free, siloxane treated, silica-modified HZSM-5 tested under the same operating conditions.

TABLE 5

| Component, wt % | Pt—$SiO_2$-HZSM-5 | $SiO_2$-HZSM-5 |
|---|---|---|
| Benzene | 46.62 | 38.43 |
| Ethylbenzene | 0.33 | 1.18 |
| Xylenes | 52.35 | 58.56 |
| $C_9$+ Aromatics | 0.70 | 1.83 |
|  | 100.00 | 100.00 |
| Ethylbenzene in $C_8$, wt % | 0.63 | 1.98 |
| p-Xylene in Xylenes, wt % | 98.4 | 98.7 |
| Toluene Conversion, wt % | 25 | 22 |

At similar toluene conversion, the ethylbenzene product was reduced by a factor of 3.6 using the Pt-catalyst while the p-xylene selectivities remained very high at 98.4%–98.7%. The undesirable $C_9$+ aromatics product was also reduced by nearly a factor of 3.

The results of Examples 6, 7 and 8, which are reported in Table 6, indicate the beneficial effect on ethylbenzene in the product stream by the addition of platinum to the catalytic molecular sieve.

EXAMPLE 6

Silicone selectivation of a 10% $SiO_2$-HZSM-5 was carried out using 1% phenylmethyl silicone in a toluene feed at 446° C., 500 psig, 4.0 WHSV, and a hydrogen/hydrocarbon ratio= 2. At 31 hours on stream the feed was changed to 100% toluene. At 52 hours on stream the temperature was increased to 468° C. and at 165 hours the WHSV was lowered to 3.0. The data at 39 days on stream are shown in column 1 of Table 6.

EXAMPLE 7

Silicone selectivation of a 0.025%Pt 10% $SiO_2$-HZSM-5 was carried out using 1% phenylmethyl silicone in a toluene feed at 446° C., 500 psig, 4.0 WHSV, and a hydrogen/hydrocarbon ratio=2. At 56 hours on stream the feed was changed to 100% toluene. At 73 hours on stream the temperature was increased to 468° C. The data at 7 days on stream are shown in column 2 of Table 6.

EXAMPLE 8

Silicone selectivation of a nitric acid activated 0.05% Pt 10% SiO$_2$-HZSM-5 was carried out using 1% phenylmethyl silicone in a toluene feed at 446° C., 500 psig, 4.0 WHSV, and a hydrogen/hydrocarbon ratio=2. At 27 hours on stream the feed was changed to 100% toluene. Temperature, WHSV, and hydrogen/hydrocarbon ratio were varied during the run. The data at 13 days on stream are shown in column 3 of Table 6.

TABLE 6

|  | Silicone | Silicone/Pt | |
| --- | --- | --- | --- |
|  | Ex. 6 | Ex. 7 | Ex. 8 |
| Reaction Conditions | | | |
| Temperature, °C. | 468 | 468 | 431 |
| Pressure, psig | 500 | 500 | 500 |
| H$_2$/HC | 2 | 2 | 8 |
| WHSV | 3 | 4 | 4 |
| Time on Stream, days | 39 | 7 | 13 |
| Toluene Conversion, wt % | 23 | 20 | 21 |
| Products, wt % | | | |
| C$_5$ | 2.5 | 2.5 | 2.5 |
| Benzene | 43.0 | 43.6 | 47.2 |
| Ethylbenzene | 1.9 | 0.2 | 0.1 |
| Xylenes | 50.4 | 53.1 | 50.0 |
| Ethyltoluenes | 1.9 | 0.5 | 0.2 |
| C$_{10}$+ | 0.3 | 0.1 | 0.0 |
|  | 100.0 | 100.0 | 100.0 |
| p-Xylene | 99.7 | 98.7 | 99.7 |
| m-Xylene | 0.3 | 1.3 | 0.3 |
| o-Xylene | tr. | tr. | tr. |
|  | 100.0 | 100.0 | 100.0 |
| Benzene/Xylenes, m/m | 1.2 | 1.1 | 1.3 |
| p-XylenePurity, wt % | 97.8 | 98.3 | 99.5 |

Example 6 through 8 indicate that the levels of ethylbenzene in the reaction products of the present invention can be reduced by using a catalytic molecular sieve with a hydrogenation/dehydrogenation function such as platinum incorporated into the catalytic molecular sieve. The level of ethylbenzene in the product stream is preferably at a commercially acceptable level of not greater than 0.3%, and is most preferably not greater than about 0.2%.

As stated above, the present invention advantageously provides a product stream having a high para-xylene purity with respect to the other C$_8$ products. Table 7 provides the relative proportions of para-xylene to various combinations of other products.

TABLE 7

| Comparison of Product Parameters CATALYST | | | | |
| --- | --- | --- | --- | --- |
|  | Silicone | Silicone/Pt | | Calculated Equilibrium |
| Parameter | Ex. 6 | Ex. 7 | Ex. 8 | Value |
| p-Xylene/EB | 26.4 | 262 | 498 | 2.5 |
| p-Xyl/EB + m,o-xyl (other C$_8$) | 23.9 | 58.2 | 166 | 2.5 |
| p-Xyl/EB + m,o-Xyl + C$_9$ (other C$_8$ + C$_9$) | 12.6 | 37.4 | 99.6 | 1.6 |
| p-Xylene purity (in all C$_8$s), wt % | 95.7 | 98.3 | 99.5 | 71.8 |
| p-Xylene yield | 10.6 | 10.6 | 10.2 | 11.9 |

TABLE 7-continued

| Comparison of Product Parameters CATALYST | | | | |
| --- | --- | --- | --- | --- |
|  | Silicone | Silicone/Pt | | Calculated Equilibrium |
| Parameter | Ex. 6 | Ex. 7 | Ex. 8 | Value |
| (based on all products and toluene), wt % | | | | |

Figure 4:
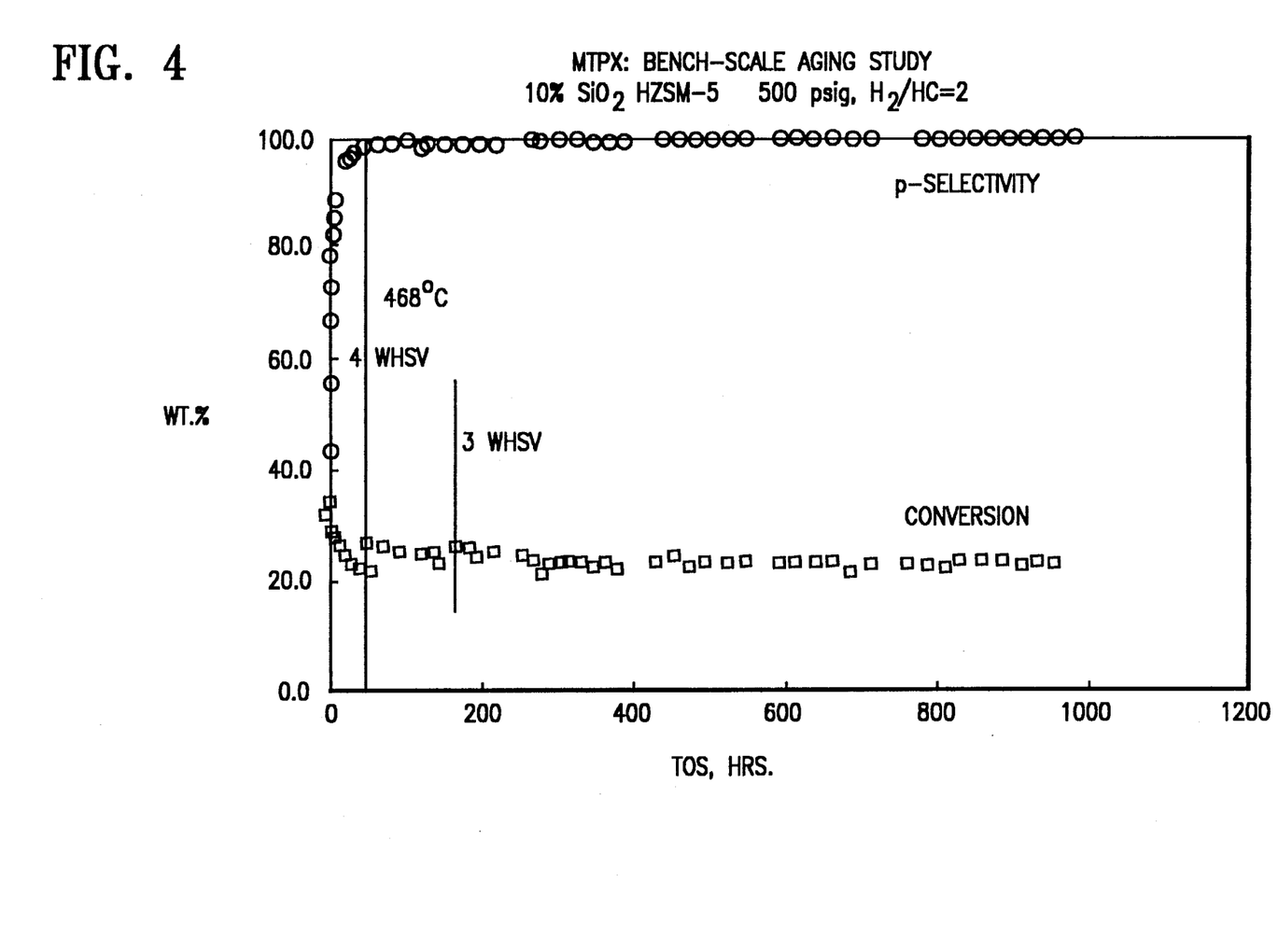
FIG. 4 provides ageing data for one embodiment of the present invention.

FIG. 4 provides the results of an ageing study of the present invention. As illustrated, the high para-selectivity and conversion rates of the present invention are achieved even at about 1000 hours on stream.

The present invention therefore provides novel processes and catalysts for increasing the para-selectivity in the selective production of para-substituted aromatic compounds. From the description provided herein, those skilled in the art will appreciate that the catalysts and processes of the present invention provide greater para-selectivity at conversion rates unattained by previously known methods.

What is claimed is:

1. A toluene disproportionation process comprising:

contacting a reaction stream comprising toluene, hydrogen and an organic silicon compound with a catalytic molecular sieve which has been pre-selectivated with a silicon-containing compound, said organic silicon compound or silicon-containing compound being selected from the group consisting of silicones, siloxanes, polysiloxanes, silanes and mixtures thereof, provided in the event that said organic silicon compound is an alkoxysilane, then said alkoxysilane has at least one silicon-hydrogen bond, said contacting taking place at reaction conditions suitable to provide a single pass para-xylene product purity, relative to all C$_8$ products, of at least about 90% and concurrently therewith at least about 15% toluene conversion.

2. A process according to claim 1 wherein said reaction stream comprises at least 80% toluene and at least 0.1% silicone compound.

3. A process according to claim 1 wherein the toluene conversion is at least 20%, and wherein a xylene product comprises at least 95% para-xylene.

4. A process according to claim 1 wherein said catalytic molecular sieve comprises a constraint index of about 1 to 30, and said reaction conditions comprise a temperature of about 350° to 540° C., a pressure of about atmospheric to 5000 psig, a WHSV of about 0.1 to 20, and a hydrogen to hydrocarbon molar ratio of about 0.1 to 20.

5. A process according to claim 1 wherein said catalytic molecular sieve includes a metal component supplying a hydrogenation-dehydrogenation function.

6. A process according to claim 5 wherein said metal comprises platinum.

7. A process according to claim 1 wherein said contacting step provides a xylene product comprising not more than 0.5% ortho-xylene and not more than 5% meta-xylene.

8. A process according to claim 1 wherein at least 20% of said toluene is converted into xylenes.

9. A process according to claim 1 wherein at least 25% of said toluene is converted into xylenes.

10. A process according to claim 1 wherein said single pass para-xylene product purity is at least 95%.

11. The process according to claim 1 wherein said organic silicon compound is not an alkoxysilane.

12. The process according to claim 1 wherein said molecular sieve is ZSM-5.

13. The process according to claim 12 wherein said ZSM-5 is combined with a silica binder derived from inorganic silicon oxide.

14. The process according to claim 1 wherein said organic silicone compound comprises a mixture of phenylmethyl silicone and dimethyl silicon.

* * * * *